US012678229B2

(12) United States Patent
Kopel et al.

(10) Patent No.: US 12,678,229 B2
(45) Date of Patent: Jul. 14, 2026

(54) SYSTEMS AND METHOD OF PLANNING THORACIC SURGERY

(71) Applicant: Covidien LP, Mansfield, MA (US)

(72) Inventors: Evgeni Kopel, Barkan (IL); Gabriella Goranov, Bat Yam (IL); Oren P. Weingarten, Hod-Hasharon (IL); Ariel Birenbaum, Raanana (IL); Ofer Barasofsky, Tel Mond (IL)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 18/026,586

(22) PCT Filed: Sep. 30, 2021

(86) PCT No.: PCT/US2021/052975
§ 371 (c)(1),
(2) Date: Mar. 15, 2023

(87) PCT Pub. No.: WO2022/072700
PCT Pub. Date: Apr. 7, 2022

(65) Prior Publication Data
US 2024/0024029 A1    Jan. 25, 2024

Related U.S. Application Data

(60) Provisional application No. 63/086,385, filed on Oct. 1, 2020.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *G06T 7/10* (2017.01); *G06T 19/20* (2013.01);
(Continued)

(58) Field of Classification Search
None
See application file for complete search history.

(56) References Cited

U.S. PATENT DOCUMENTS 10,282,841 B1 *  5/2019  Parsons-Wingerter .....................
                                          G06T 7/0014
2005/0033117 A1 *  2/2005  Ozaki .................... G16H 40/63
                                          600/117
(Continued)

FOREIGN PATENT DOCUMENTS

EP          3298976 A1      3/2018
EP          3372185 A1      9/2018
(Continued)

OTHER PUBLICATIONS

Johny A. Verschakelen and Walter de Wever: "Computed Tomography of the Lung : A Pattern Approach", Mar. 5, 2007 (Mar. 5, 2007) , Springer Berlin / Heidelberg, XP002806239.
(Continued)

*Primary Examiner* — Andrew G Yang
(74) *Attorney, Agent, or Firm* — Weber Rosselli & Cannon LLP

(57) ABSTRACT
Systems and method of planning thoracic surgery. A three-dimensional model is generated to provide greater clarity between lung segments as well as identifying the airways and vasculature supporting the lung segment to enable accurate surgical planning.

18 Claims, 16 Drawing Sheets

(51) Int. Cl.
    *G06T 7/10*          (2017.01)
    *G06T 19/20*       (2011.01)

(52) U.S. Cl.
    CPC ... *A61B 2034/105* (2016.02); *A61B 2034/107*
        (2016.02); *G06T 2207/10081* (2013.01); *G06T*
               *2207/30101* (2013.01); *G06T 2210/41*
          (2013.01); *G06T 2219/028* (2013.01); *G06T*
                       *2219/2021* (2013.01)

(56) References Cited

U.S. PATENT DOCUMENTS

| | | | | |
|---|---|---|---|---|
| 2006/0089624 | A1* | 4/2006 | Voegele | A61B 34/20 |
| | | | | 606/1 |
| 2006/0159328 | A1* | 7/2006 | Vaz | G06T 7/11 |
| | | | | 382/173 |
| 2009/0116718 | A1* | 5/2009 | Goto | A61B 5/055 |
| | | | | 382/131 |
| 2012/0041739 | A1* | 2/2012 | Taylor | A61B 5/02007 |
| | | | | 382/128 |
| 2014/0105472 | A1* | 4/2014 | Yin | G06T 7/0012 |
| | | | | 382/128 |
| 2014/0320500 | A1* | 10/2014 | Fletcher | H04L 43/045 |
| | | | | 345/440 |
| 2014/0341426 | A1* | 11/2014 | Wu | G06T 7/187 |
| | | | | 382/103 |

| | | | | |
|---|---|---|---|---|
| 2016/0005220 | A1* | 1/2016 | Weingarten | A61B 34/10 |
| | | | | 382/131 |
| 2016/0063721 | A1* | 3/2016 | Nakano | G06T 7/10 |
| | | | | 382/173 |
| 2016/0157807 | A1* | 6/2016 | Anderson | A61B 6/032 |
| | | | | 600/407 |
| 2017/0348067 | A1* | 12/2017 | Krimsky | A61B 5/066 |
| 2018/0121627 | A1* | 5/2018 | Tavana | B29C 64/124 |
| 2018/0235713 | A1* | 8/2018 | Krimsky | A61B 34/10 |
| 2020/0030044 | A1* | 1/2020 | Wang | A61B 34/10 |
| 2020/0081604 | A1* | 3/2020 | Delfino | G06F 3/04845 |
| 2020/0371665 | A1* | 11/2020 | Clausen | G06F 3/017 |
| 2021/0196423 | A1* | 7/2021 | Shelton, IV | A61B 90/361 |

FOREIGN PATENT DOCUMENTS

| | | | | |
|---|---|---|---|---|
| EP | 3811887 | A1 | 4/2021 | |
| WO | 2009138871 | A2 | 11/2009 | |
| WO | 2016069324 | A1 | 5/2016 | |
| WO | WO-2020186015 | A1 * | 9/2020 | A61B 34/25 |
| WO | 2021105785 | A1 | 6/2021 | |

OTHER PUBLICATIONS

Partial European Search Report issued in European Patent Application No. 22203063.7 dated Mar. 20, 2023.
PCT Search Report and Written Opinion issued in PCT/US2021/052975 dated May 9, 2022.

* cited by examiner

410

402

250

SYSTEMS AND METHOD OF PLANNING THORACIC SURGERY

CROSS-REFERENCE TO RELATED APPLICATIONS

This application is a 371 application of PCT/US2021/052975 filed Sep. 30, 2021 which claims benefit of and priority to U.S. Patent Application Ser. No. 63/086,385 filed Oct. 1, 2020, the disclosures of the above-identified applications are hereby incorporated by reference in their entirety.

FIELD

This disclosure is directed to systems and method of planning thoracic surgery. In particular, the disclosure is directed to a software application configured to generate three-dimensional models from computed tomography and other image type data sets.

BACKGROUND

During a surgical procedure, clinicians often use CT images for determining a plan or pathway for navigating through the luminal network of a patient. Absent software solutions, it is often difficult for the clinician to effectively plan a pathway based on CT images alone. This challenge in creating paths to certain targets is especially true in the smaller branches of the bronchial tree where CT images typically do not provide sufficient resolution for accurate navigation.

While the software solutions for pathway planning a pathway through the luminal networks of, for example the lungs, are great for their intended purpose, they do not assist the clinicians in planning for thoracic surgeries. Thoracic surgeries are typically performed laparoscopically or via open surgery through the patient's chest. Lobectomies are one such thoracic procedure and is one where an entire lung lobe is removed. One reason for performing a lobectomy is that the lobes of the lung are readily discernable and separated from one another via a fissure. As a result, the vasculature of the lobe is also relatively distinct and can be planned for and can be addressed during the surgery with reasonable certainty. However, in many instances a lobectomy removes too much tissue, particularly healthy lung tissue. This can be critical in determining whether a patient is even a candidate for surgery.

Each lung lobe is composed of either three or four lung segments. These segments are generally independently vascularized. This means that if the individual segments can be identified, and the vasculature related to the segments distinguished from other lobes, a segmentectomy may be undertaken. A segmentectomy procedure can increase the number of patients that are surgical candidates because it enables the surgeon to remove the diseased tissue while leaving all other tissue. The problem with segmentectomy procedures is that while they are more tissue efficient, determining the locations of the relevant vascular structures can be very challenging even for highly trained professionals.

The instant disclosure is directed to addressing the shortcomings of current imaging and planning systems.

SUMMARY

One aspect of the disclosure is directed to receiving computed tomography (CT) image data. The receiving also includes receiving an indication of a location of a target in the CT image data. The receiving also includes generate a three-dimensional model (3D) from the CT image data. The receiving also includes receiving a selection of a generation level. The receiving also includes removing from a representation of the 3D model in a user interface the generations beyond the selected generation level. The receiving also includes receiving a selection of a crop tool. The receiving also includes presenting a region around a target. The receiving also includes receiving a change in the region around the target. The receiving also includes identifying all airways and blood vessels of the 3D model entering the changed region and all preceding airways and blood vessels directly connected to the airways and blood vessels in the 3D model to form identified airways and blood vessels. The receiving also includes removing from the 3D model all airways and blood vessels other than the identified airways and blood vessels.

Another aspect of the disclosure is directed to a method of planning a thoracic surgery including: receiving computed tomography (CT) image data; generating a three-dimensional model (3D) from the CT image data; receiving a selection of a crop tool; presenting a region around a target; identifying all airways and blood vessels of the 3D model entering the region and all preceding airways and blood vessels directly connected to the airways and blood vessels entering the region in the 3D model; and removing from the 3D model all airways and blood vessels other than the identified airways and blood vessels; and displaying the 3D model in a user interface, where the 3D model includes only the identified airways and blood vessels. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including receiving an indication of a location of a target in the CT image data. The method further including receiving a selection of a generation level and removing generations from the 3D model beyond the selected generation level. The method further including determining a generation by identifying a bifurcation of an airway or blood vessel and determining a diameter of an airway or blood vessel leading to the bifurcation and a diameter of airways or blood vessels extending beyond the bifurcation, where one of the airways or blood vessels extending from the bifurcation is considered the same generation as the airway or blood vessel leading to the bifurcation when the determined diameters are similar in size. The method further including determining that an airway or blood vessel extending from a bifurcation is at a next generation when that airway or blood vessel's diameter less than 50% of the diameter of the airway or blood vessel leading to the bifurcation. The method further including receiving a change in shape of the region around the target. The method further including capturing a screenshot. The method further including at least one CT image, where the CT image is tied to the 3D model such that manipulation of the 3D model results in corresponding changes to the display of the CT image. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a thoracic surgery planning system including: a processor, a display in communication with the processor. The thoracic surgery planning system also includes a memory in communication with the processor, where the memory stores therein executable code that when executed by the processor generate a user interface (UI) for display on the display, the user interface including, a three-dimensional (3D) model of airways and vasculature of a patient's lungs, at least one generation tool configured to limit a number of generations of the 3D model displayed, a margin tool configured to adjust a displayed margin around a target, and a plurality of orientation manipulation tools configured to alter the view of the 3D model presented in the UI. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The thoracic surgery planning system where the memory is configured to receive CT image scan data and the processor is configured executed code stored in the memory to generate the 3D model from the CT image scan. The thoracic surgery planning system where the UI includes an orientation compass identifying axial, coronal, and sagittal planes of 3D model. The thoracic surgery planning system further including an anchoring tool, where the anchoring tool enables placement of the orientation compass on or near the 3D model to define a point of rotation of the 3D model. The thoracic surgery planning system further including a single axis rotation tool, where when one of the axes in the single axis selection to is selected, all further inputs to rotate the 3D model achieve rotation only about the selected axis. The thoracic surgery planning system further including a zoom tool, where the zoom tool depicts a relative size of the presented model in the UI compared to full size. The thoracic surgery planning system where the zoom tool also enables panning of the 3D model in the UI. The thoracic surgery planning system further including a crop tool, where when selected a region is depicted around the target. The thoracic surgery planning system where the region is adjustable such that segments of airways or blood vessels are included or excluded from the region. The thoracic surgery planning system where when the crop is executed the processor executes code to determine the airways or blood vessels which are within the region and any of their preceding airways or blood vessels, and the 3D model is updated to eliminate all airways or blood vessels except for the identified airways or blood vessels. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Yet a further aspect of the disclosure is directed to a method of planning a thoracic surgery including: receiving computed tomography (CT) image data; generating a three-dimensional model (3D) from the CT image data; receiving a selection of a generation level and removing generations of airways and blood vessels from the 3D model beyond the selected generation level; and displaying the 3D model in a user interface, where the 3D model includes only the selected generations of airways and blood vessels. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including determining a generation by identifying a bifurcation of an airway or blood vessel and determining a diameter of an airway or blood vessel leading to the bifurcation and a diameter of airways or blood vessels extending beyond the bifurcation, where one of the airways or blood vessels extending from the bifurcation is considered the same generation as the airway or blood vessel leading to the bifurcation when the determined diameters are similar in size. The method further including determining that an airway or blood vessel extending from a bifurcation is at a next generation when that airway or blood vessel's diameter less than 50% of the diameter of the airway or blood vessel leading to the bifurcation. The method further including receiving an indication of a location of a target in the CT image data. The method further including receiving a selection of a crop tool and presenting a region around a target. The method further including identifying all airways and blood vessels of the 3D model entering the region and all preceding airways and blood vessels directly connected to the airways and blood vessels entering the region in the 3D model. The method further including removing from the 3D model all airways and blood vessels other than the identified airways and blood vessels. The method may also include displaying the 3D model in a user interface, where the 3D model includes only the identified airways and blood vessels. The method further including receiving a change in shape of the region around the target. The method further including capturing a screenshot. The method further including displaying at least one CT image, where the CT image is tied to the 3D model such that manipulation of the 3D model results in corresponding changes to the display of the CT image. The method further including segmenting airways and blood vessels in the CT image data to generate the 3D model. The method further including segmenting airways and blood vessels in the CT image data to generate the 3D model. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

This disclosure is directed to a system and method of receiving image data and generating 3D models from the image data. In one example, the image data is CT image data, though other forms of image data such as Magnetic Resonance Imaging (MM), fluoroscopy, ultrasound, and others may be employed without departure from the instant disclosure.

Figure 1A:
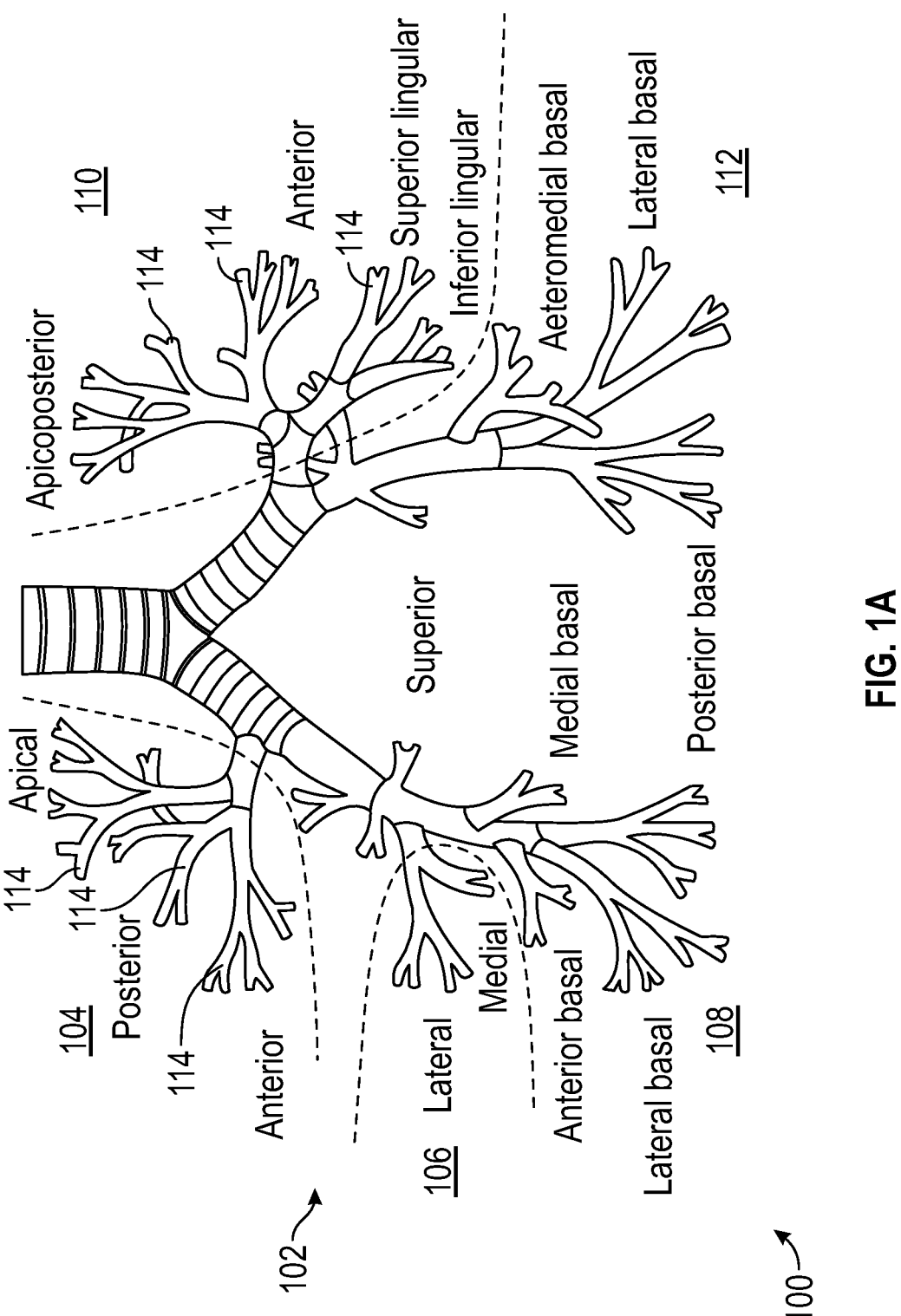
FIG. 1A is a schematic view of human lungs separated by lobes and segments.
Figure 1B:
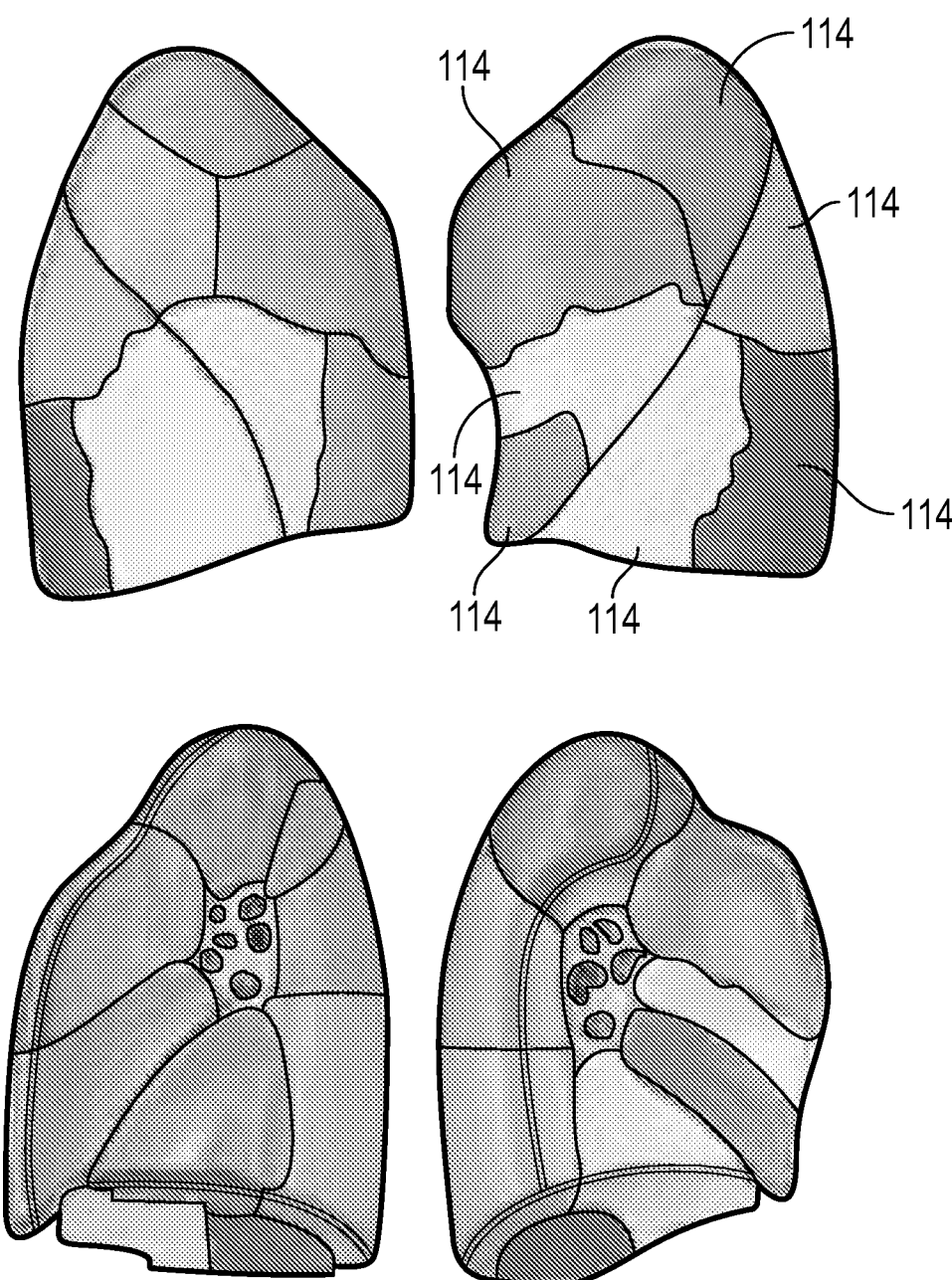
FIG. 1B is a schematic view of human lungs separated into segments.

FIG. 1A depicts a schematic diagram of the airways of the lungs 100. As ca be seen right lung 102 is composed of three segments, the superior lobe 104, middle lobe 106, and inferior lobe 108. The left lung is comprised of the superior lobe 110 and the inferior lobe 112. Each lobe 104-112 is composed of three or four segments 114, each segment 114 includes a variety of distinct airways 116. FIG. 1B depicts the right and left lungs and with each of the segments 114 as they generally appear in the human body.

As is known to those of skill in the art, the vasculature of the lungs generally follows the airways until reaching the periphery of the lungs where the blood-air barrier (alveolar-capillary barrier) where gas exchange occurs allowing carbon dioxide to be eliminated from the blood stream and oxygen to enter the blood stream as part of normal respiration. However, while the vasculature generally follows the airways, it there are instances where portions of the same blood vessel supplies two or more segments. Particularly the more central vasculature can be expected to supply multiple segments.

Further, in instances where the segmentectomy is the result of a tumor, the tumor, which is a very blood rich tissue, is fed by multiple blood vessels. These blood vessels may in fact be supplying blood to the tumor from different segments of the lungs. As a result, it is critical that the thoracic surgeon be able to identify all of the blood vessels entering the tumor and ensure that they are either sutured closed prior to resection or that a surgical stapler is employed to ensure limit the possibility of the surgeon experiencing an unexpected bleeding blood vessel during the procedure.

Figure 2:
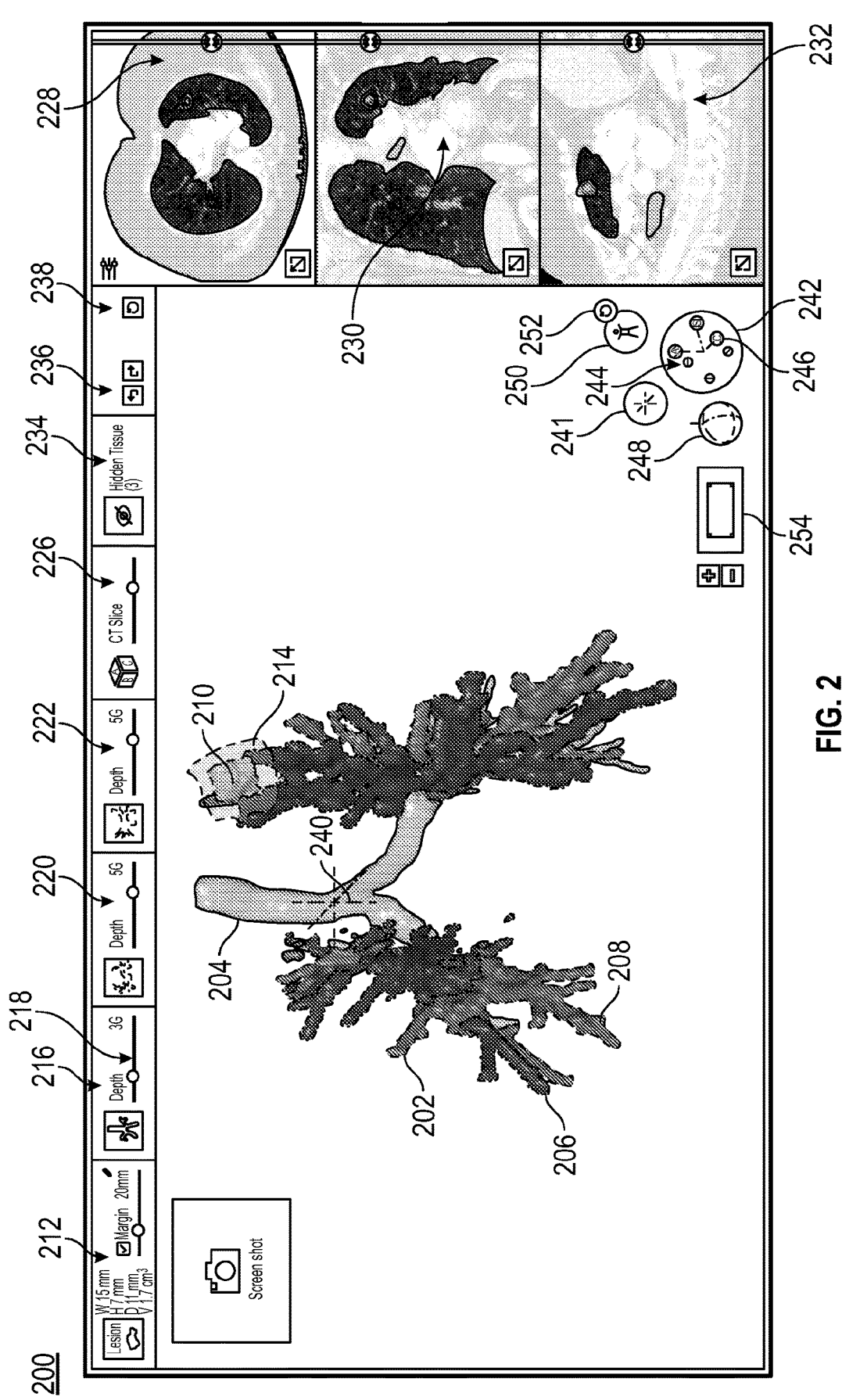
FIG. 2 is a user interface for a thoracic surgery planning platform in accordance with the disclosure.

FIG. 2 depicts a user interface 200 of a thoracic surgery planning system. The surgical planning system includes a software application stored in a memory that when executed by a processor performs a variety of steps as described hereinbelow to generate the outputs displayed in the user interface 200. As depicted in the center of the user interface 200 one of the first steps of the software is to generate a 3D model 202. The 3D model 202 is of the airways and the vasculature around the airways is generated from a CT image dataset acquired of the patient's lungs. Using segmentation techniques the 3D model 202 is defined from the CT image data set and depicts the airways 204 in one color, the veins 206 in a second color, and the arteries 208 in a third color to assist the surgeon in distinguishing the portions of the anatomy based on color.

The application generating the 3D model 202 may include a CT image viewer (not shown) enabling a user to view the CT images (e.g., 2D slice images from the CT image data) prior to generation of the 3D model 202. By viewing the CT images the clinician or other user may utilize their knowledge of the human anatomy to identify one or more tumors in the patient. The clinician may mark the position of this tumor or suspected tumor in the CT images. If the tumor is identified in for example an axial slice CT image, that location may also be displayed in for example sagittal and coronal views. The user may then adjust the identification of edges of the tumor in all three views to ensure that the entire tumor is identified. As will be appreciated, other views may be viewed to assist in this process without departing from the scope of the disclosure. The application utilizes this indication of location provided by the clinician to generate and display an indicator of the location of the tumor 210 in the 3D model 202. In addition to manual marking of the location of the tumor, there are a variety of known automatic tumor identification tools that are configured to automatically process the CT image scan and to identify the suspected tumors.

The user interface 200 includes a variety of features that enable the clinician to better understand the physiology of the patient and to either enhance or reduce the volume of information presented such that the clinician is better able to understand. A first tool is the tumor tool 212 which provides information regarding the tumor or lesion that was identified in the 2D CT image slices, described above. The tumor tool 212 provides information regarding the tumor such as its dimensions. Further, the tumor tool 212 allows for creation of a margin 214 around the tumor 210 at a desired distance from edges of the tumor 210. The margin 214 identifies that portion of healthy tissue that should be removed to ensure that all of the cancerous or otherwise diseased tissue is removed to prevent future tumor growth. In addition, by providing an indicator of the margin 214, the user may manipulate the 3D model 202 to understand the vasculature which intersects the tumor 210. Since tumors are blood rich tissue there are often multiple blood vessels which lead to or from the tumor. Each one of these needs to be identified and addressed during the segmentectomy procedure to ensure complete closure of the blood vessels serving the tumor. Additionally, the margin may be adjusted to or changed to limit the impact of the procedure on adjacent tissue that may be supplied by common blood vessels. For example, the margin is reduced to ensure that only one branch of a blood vessel is transected and sealed, while the main vessel is left intact so that it can continue to feed other non-tumorous tissue. The identification of these blood vessels in an important feature of the disclosure.

The next tool depicted in FIG. 2 is an airway generation tool 216. The airway generation tool 216 allows the user to determine how many generations of the airways are depicted in the 3D model 202. As will be appreciated, image processing techniques have developed to allow for the identification of the airways throughout the lung tissue. There are up to about 23 generations of airway in the lungs of a human from the trachea to the alveolar sacs. However, while very detailed 3D models can be generated, this detail only adds to the clutter of the 3D model and renders the model less useful to the user as the structures of these multiple generations obscures structures. Thus, the airway generation tool 216 allows the user to limit the depicted generations of the airways to a desired level that provides sufficient detail for the planning of a given procedure. In FIG. 2 the airway generation tool 216 is set to the third generation, and a slider 218 allows for the user to alter the selection as desired.

Both a venous blood vessel generation tool 220 and an arterial blood vessel generation tool 222 are depicted in FIG. 2. As with the airway generation tool 216, the venous blood vessel generation tool 220 and the arterial blood vessel generation tool 222 allow the user to select the level of generations of veins and arteries to depict in the 3D model. Again, by selecting the appropriate level of generation the 3D model 202 may be appropriately decluttered to provide useable information to the user.

While these blood vessel generation tools 220 and 222 and the airway generation tool 216 are described here as being a global number of generations of blood vessels and airways displayed in the 3D model 202, they may also be employed to depict the number of generations distal to a given location or in an identified segment of the 3D model 202. In this manner the clinician can identify a particular branch of an airway or blood vessel and have the 3D model 202 updated to show a certain number of generations beyond an identified point in that airway or blood vessel.

In accordance with the disclosure, a generation algorithm has been developed to further assist in providing useful and clear information to the clinician when viewing 3D models having airways and blood vessels both displayed in the UI 200. Traditionally in a luminal network mapping each bifurcation is treated as creation of a new generation of the luminal network. The result is that a 3D model 202 may have up to 23 generations of, for example, the airways to the alveolar sacs. However, in accordance with one aspect of the disclosure a generation is defined differently by the software application generating the 3D model. The application employs a two-step model. The first step identifies the bifurcation in a luminal network. In a second step, at the bifurcation both subsequent branching lumens are measured and if one of the branching lumens has a diameter that is similar in size to the lumen leading to the bifurcation, that branching lumen segment is considered the same generation as the preceding segment. As an example a branching lumen of "similar size" is one that is at least 50% of the size of the lumen leading to the bifurcation. The result is that a clearer indication of the luminal network from the root lumen is depicted in the 3D model at lower levels of generation. Again, this eliminates much of the clutter in the 3D model providing better actionable data for the clinician.

Additional features of the user interface 200 include a CT slice viewer 226. When selected, as shown in FIG. 2, three CT slice images 228, 230, and 232 are depicted in a side bar of the user interface 200. Each of these CT slice images includes its own slider allowing the user to move alter the image displayed along one of three axes (e.g., axial, coronal, and sagittal) of the patient to view portions of the patient's anatomy. The features identified in the 3D model 202 including airways, venous blood vessels, and arterial blood vessels are also depicted in the CT slice images to provide for greater context in viewing the images. The CT slice images may also be synchronized with the 3D model 202, allowing the user to click on any point in the 3D model 202 and see where that point is located on the CT views. This point will actually be centered in each of the CT slice images 228, 230, and 232. Further, this synchronization allows the user to click on any branch in the 3D model 202 and see where that branch is located on the CT slice images 228, 230, 232. An expand icon 233 in the lower left-hand corner of each CT slice image 228, 230, 232 allows the CT slice image to replace the 3D model 202 in the main display area of the user interface 200.

A hidden tissue feature 234 allows for tissue that is hidden from the viewer in the current view of the 3D model 202 to be displayed in a ghosted or outlined form. Further, toggles 236, and 238 allow for the 3D model 202 to be flipped or rotated.

As described herein there are a variety of tools that are enabled via the UI 200. These tools may be in the form of individual buttons that appear on the UI 200, in a banner associated with the UI 200, or as part of a menu that may appear in the UI 200 when right or left clicking the UI 200 or the 3D model 202. Each of these tools or the buttons associated with this is selectable by a user employing the pointing device to launch features of the application described herein.

Additional features of the user interface 200 include an orientation compass 240. The orientation compass provides for an indication of the orientation of the three primary axes (axial, sagittal, and coronal) with respect to the 3D model. As shown the axes are defined as axial in green, sagittal in red, and coronal in blue. An anchoring tool 241 when selected by the user ties the pointing tool (e.g., mouse or finger on touch screen) to the orientation compass 240. The user then may use a mouse or other pointing tool move the orientation compass 240 to a new location in the 3D model and anchor the 3D model 202 in this location. Upon release of the pointing tool, the new anchor point is established and all future commands to manipulate the 3D model 202 will be centered on this new anchor point. The user may then to drag one of the axes of the orientation compass 240 to alter the display of the 3D models 202 in accordance with the change in orientation of the axis selected.

Figure 16:
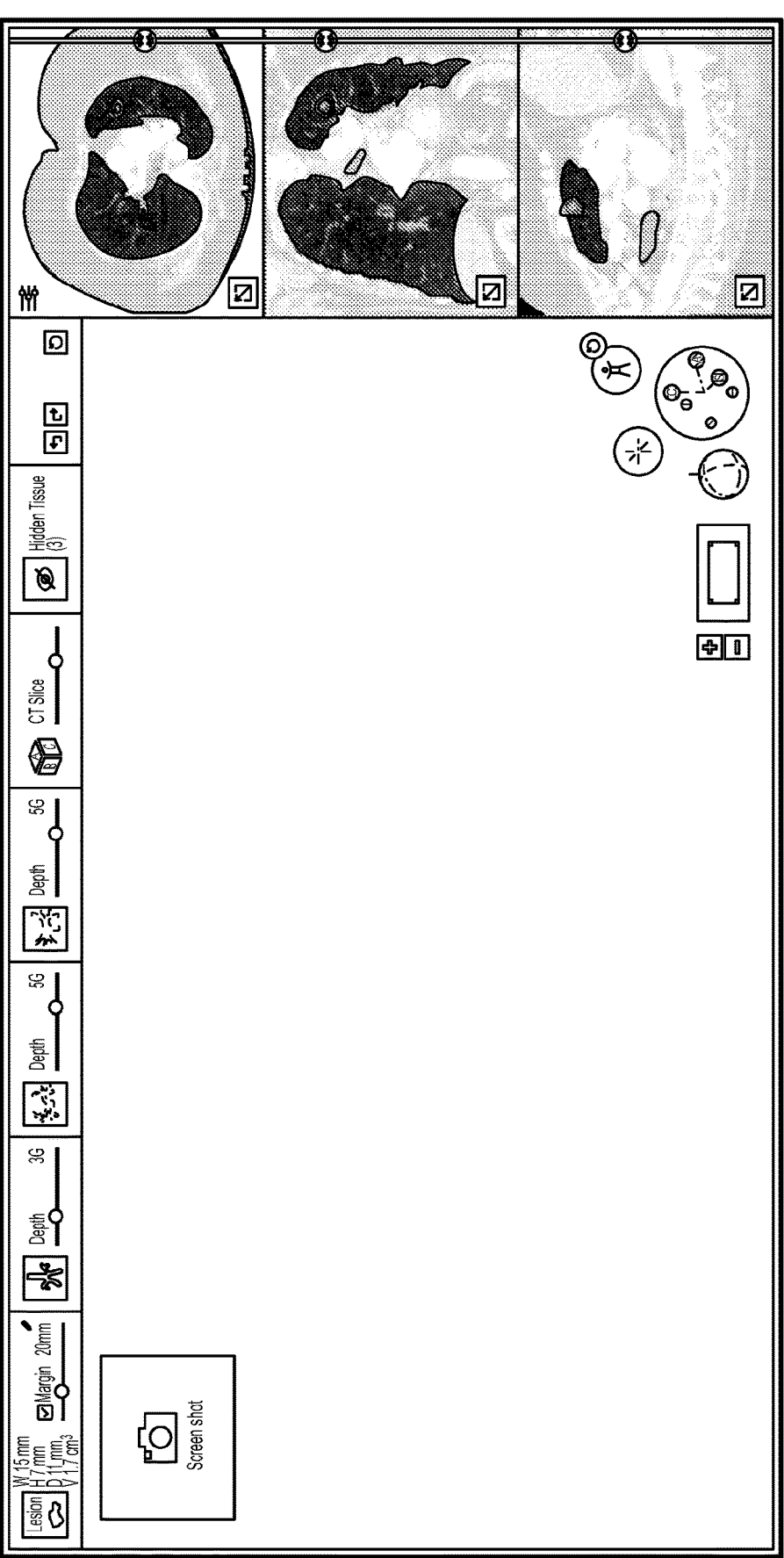
FIG. 16 depicts a user interface with the sagittal dot of the axial tool selected.
Figure 17:
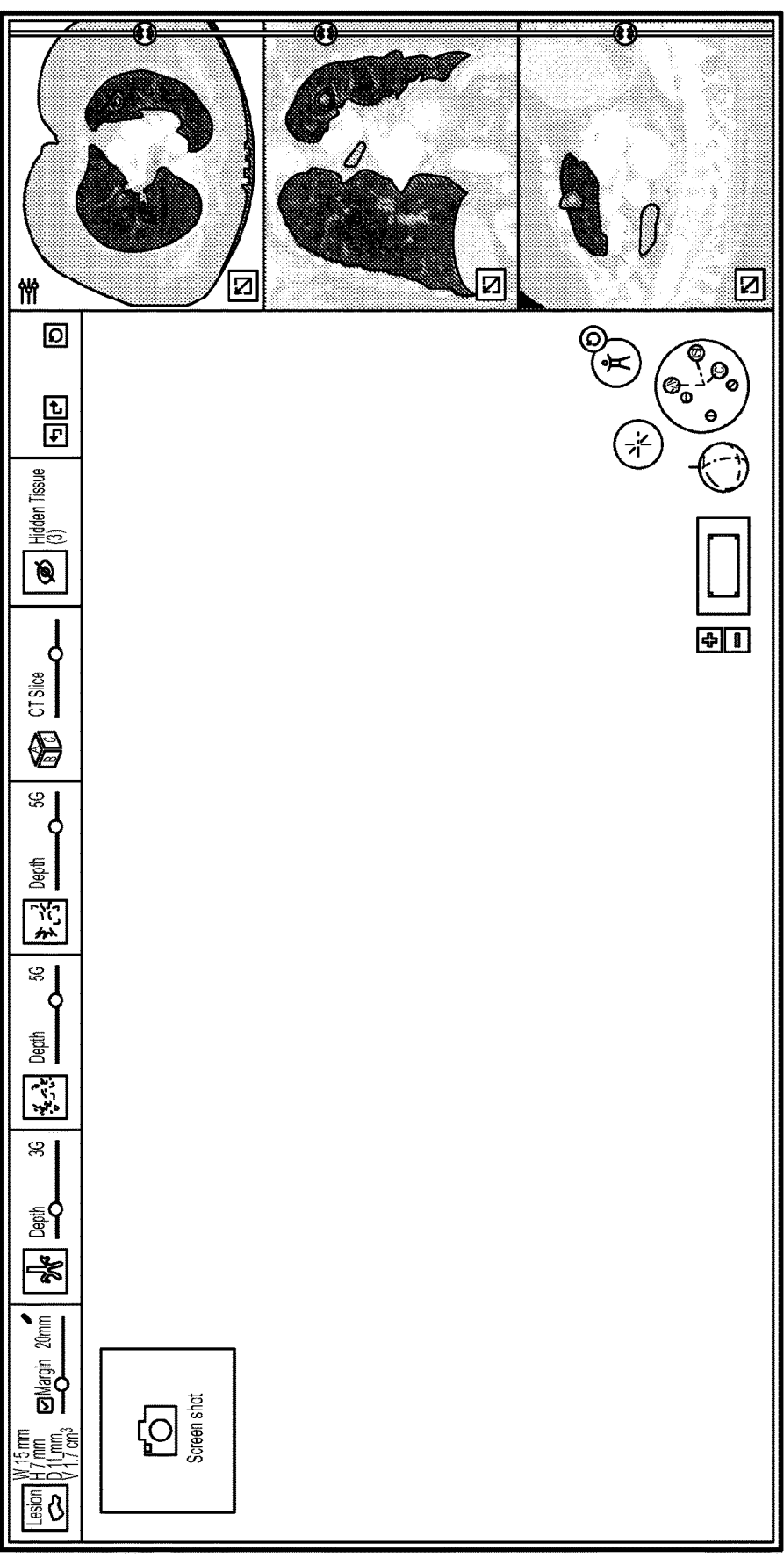
FIG. 17 depicts a user interface with the coronal dot of the axial tool selected.
Figure 18:
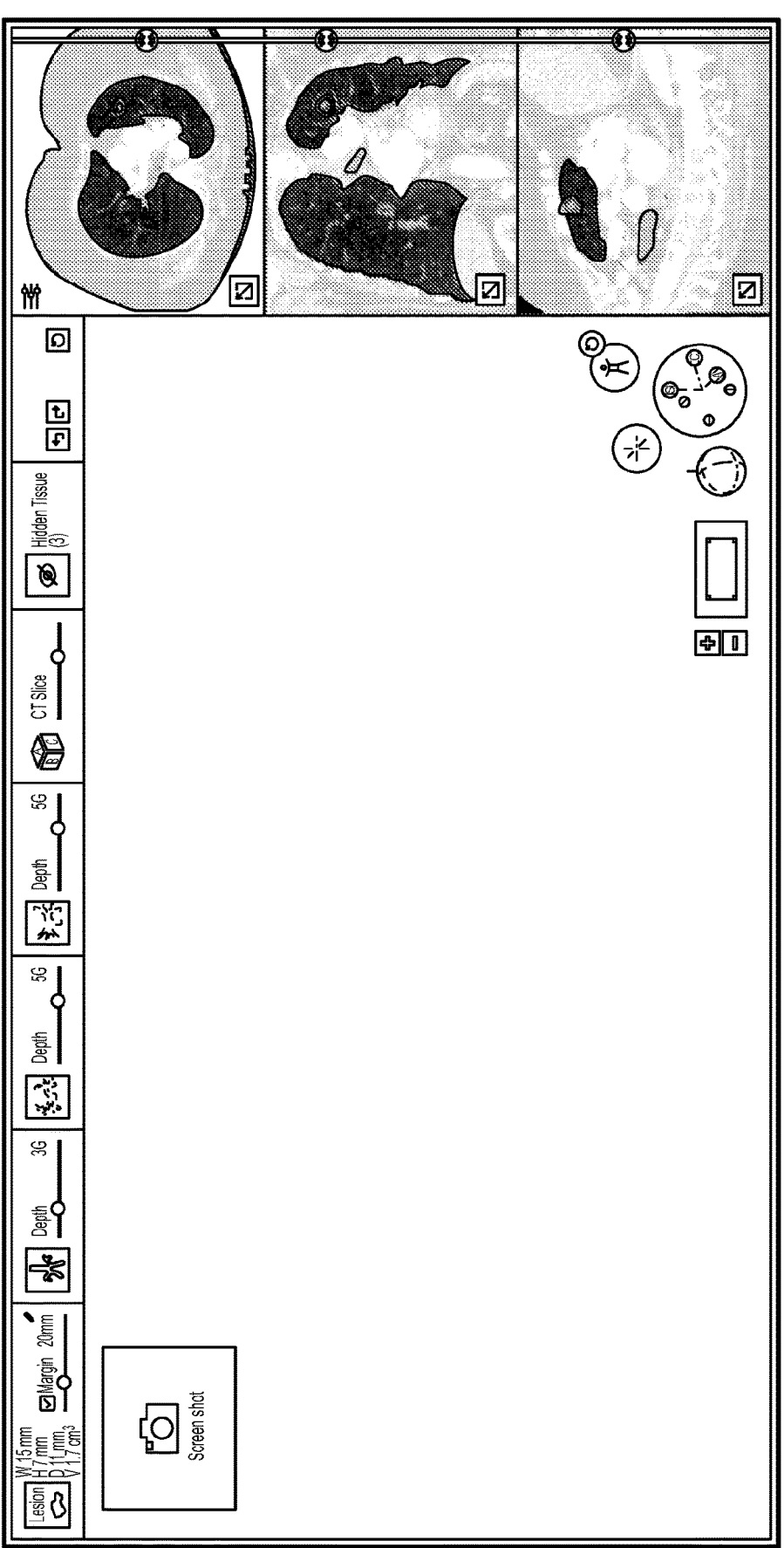
FIG. 18 depicts a user interface with the axial dot of the axial tool selected.

A related axial tool 242 is can also be used for to change the depicted orientation of the 3D model. As shown axial tool 242 includes 3 axes axial (A), sagittal (S), coronal (C). Though shown with the axes extending just to a common center point the axes extend through to the related dot 244 opposite the dot with the lettering 246. By selecting any of the lettered or unlettered dots the 3D model be rotated automatically to the view along that axis from the orientation of the dot 244 or 246. Alternatively, any of the dots 244, 246 may be selected and dragged and the 3D model 200 will alter its orientation to the corresponding viewpoint of the selected dot. In this way the axial tool 242 can be used in both free rotation and snap modes. FIGS. 16-18 depict the change in position of each of the S, C, A dots 246 are selected by the user, and the related dots 244.

A single axis rotation tool 248 allows for selection of just a single axis of the three axes shown in the orientation compass 240 and by dragging that axis in the single axis rotation tool 248, rotation of the 3D model 202 is achieved about just that single axis. Which is different than the free rotation described above, where rotation of one axis impacts the other two depending on the movements of the pointing device.

A 3D model orientation tool 250 depicts an indication of the orientation of the body of a patient relative to the orientation of the 3D model 202. A reset button 252 enables the user to automatically return the orientation of the 3D model 202 to the expected surgical position with the patient lying on their back.

Figure 19:
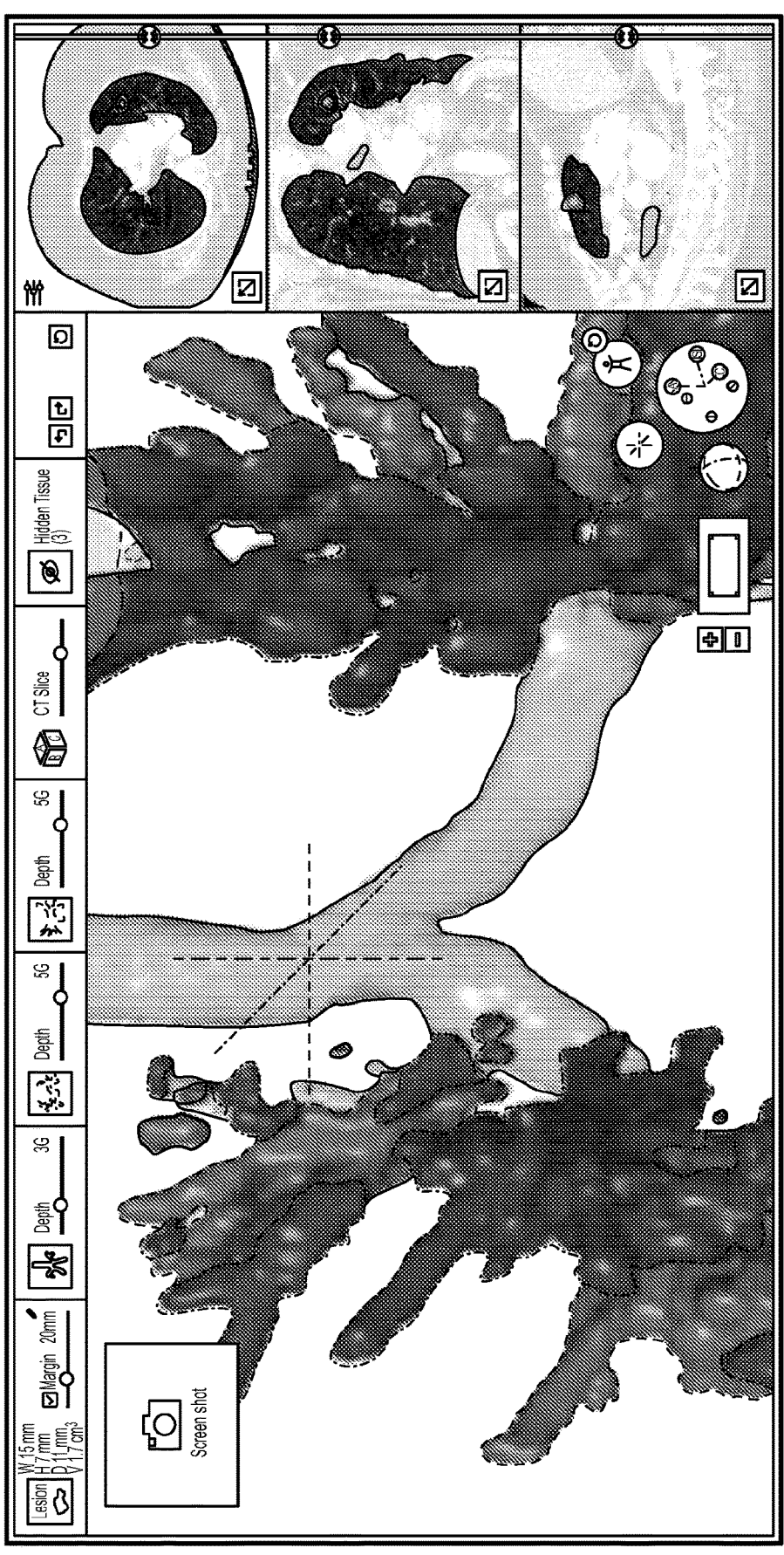
FIG. 19 depicts a user interface with the zoom indicator showing the level of zoom.
Figure 20:
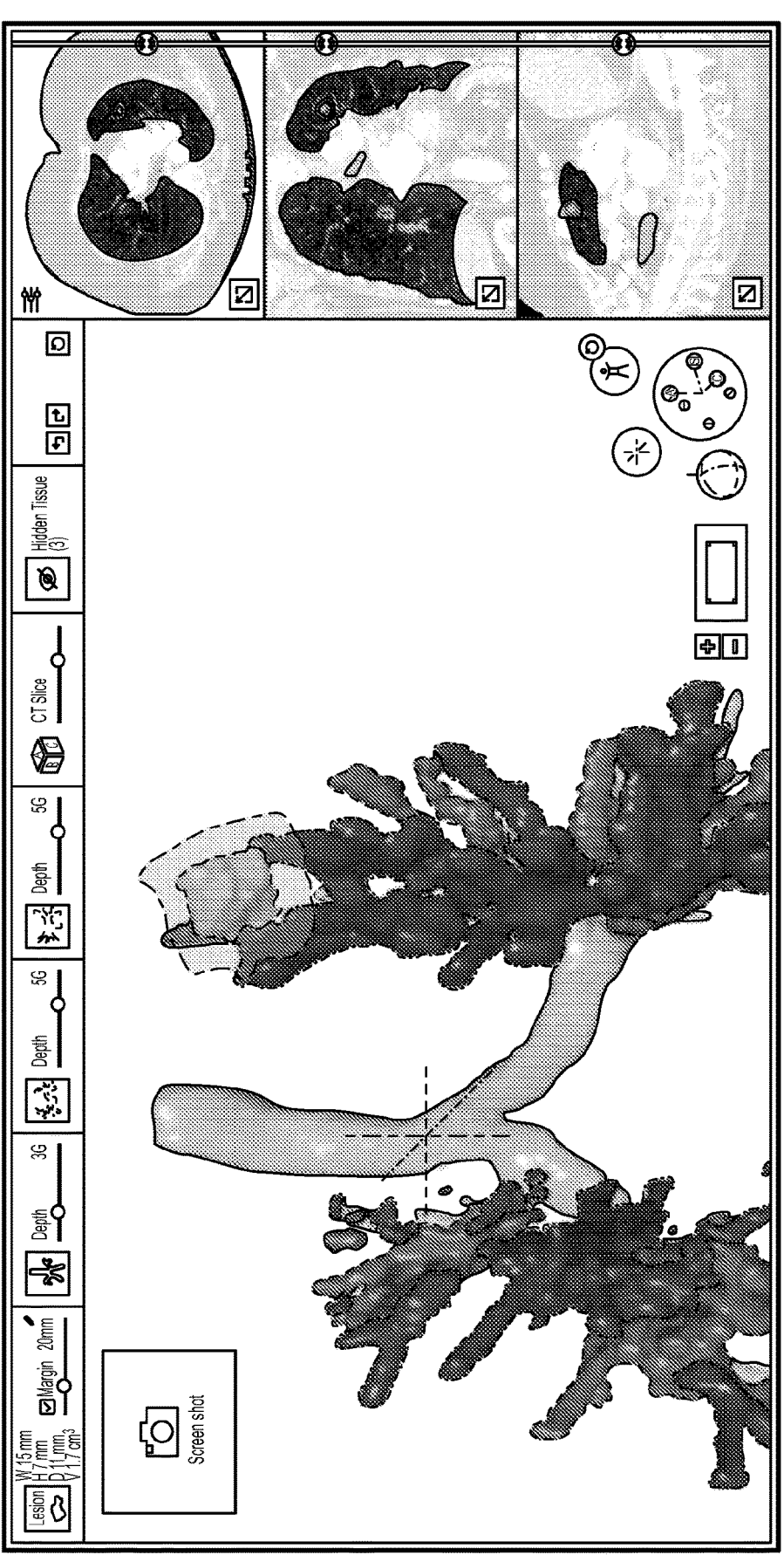
FIG. 20 depicts a user interface with the zoom indicator indicating a level of pan of the 3D model.

A zoom indicator 254 indicates the focus of the screen. By default, the inner white rectangle will be the same size as the outer grey rectangle. As the user zooms in on the 3D model 202, the relative size of the white rectangle to the grey indicates the level of zoom. In addition, once zoomed in, the user may select the white rectangle and drag it left or right to pan the view of the 3D model displayed in the user interface 200. The inner white rectangle can also be manipulated to adjust the level of the zoom. The plus and minus tags can also be used to increase or decrease the level of zoom. FIG. 19 depicts the change in the indicator 254 when the view is zoomed in. FIG. 20 depicts the change in the zoom indicator 254 depicting a panning right of the 3D model with the inner white rectangle offset to the right in the grey rectangle.

Figure 3:
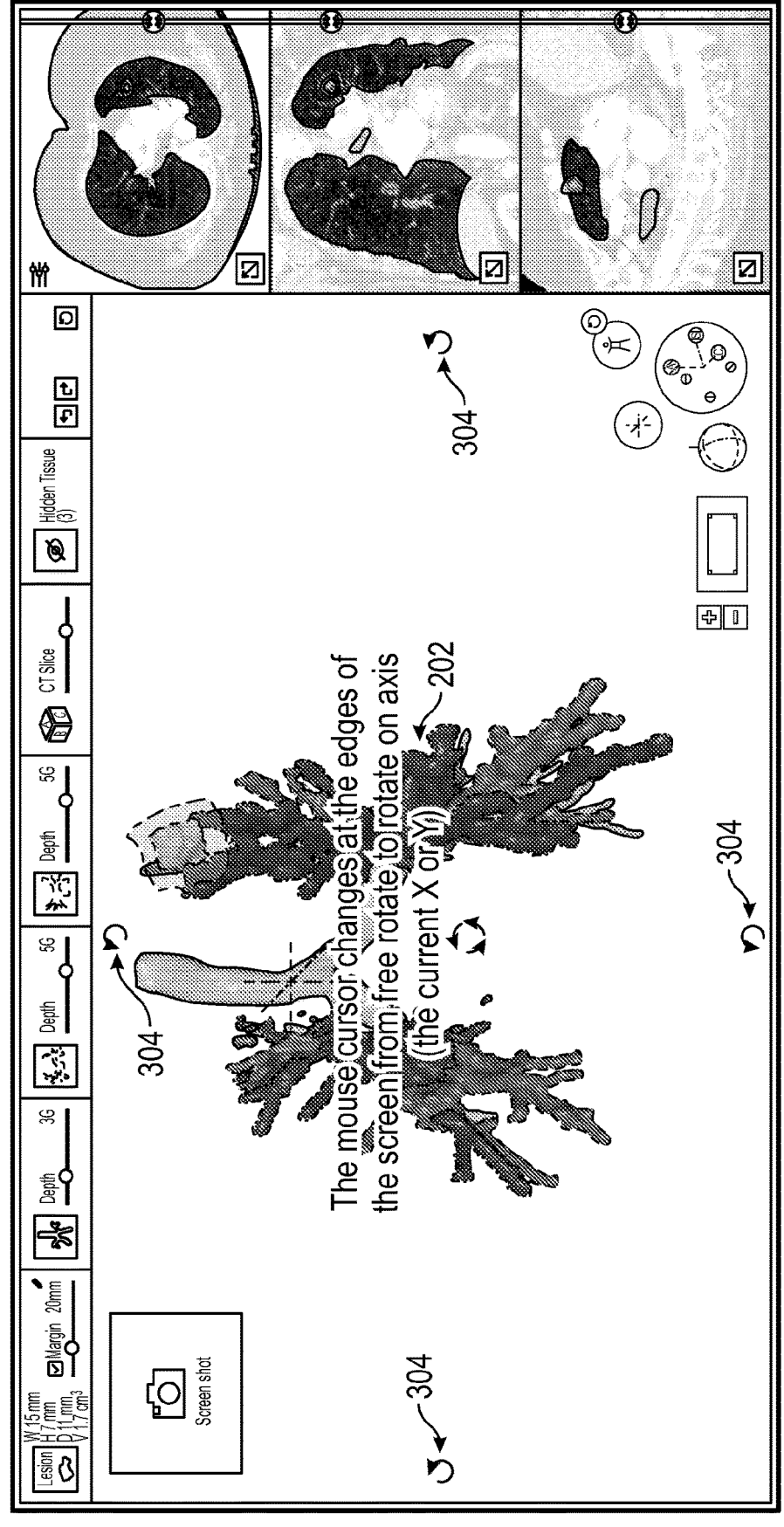
FIG. 3 is a user interface for a thoracic surgery planning platform in accordance with the disclosure.

FIG. 3 depicts a further aspect of control of the user interface 200 and particularly the model 202 displayed therein. As shown in FIG. 3, another way to rotate the 3D model 202 in a specific axis is to move the pointing device to the edges of the screen. When this is accomplished an overlay 302 is depicted showing four rotational cues 304. Selecting one of these rotation cues 304 will cause the 3D model 202 to rotate. Additionally, moving the model (i.e., pan) can also be accomplished in this overlay. Further, the pointing device may be used to identify a new spot on or near the 3D model 202 about which to rotate the 3D model 202.

Figure 4:
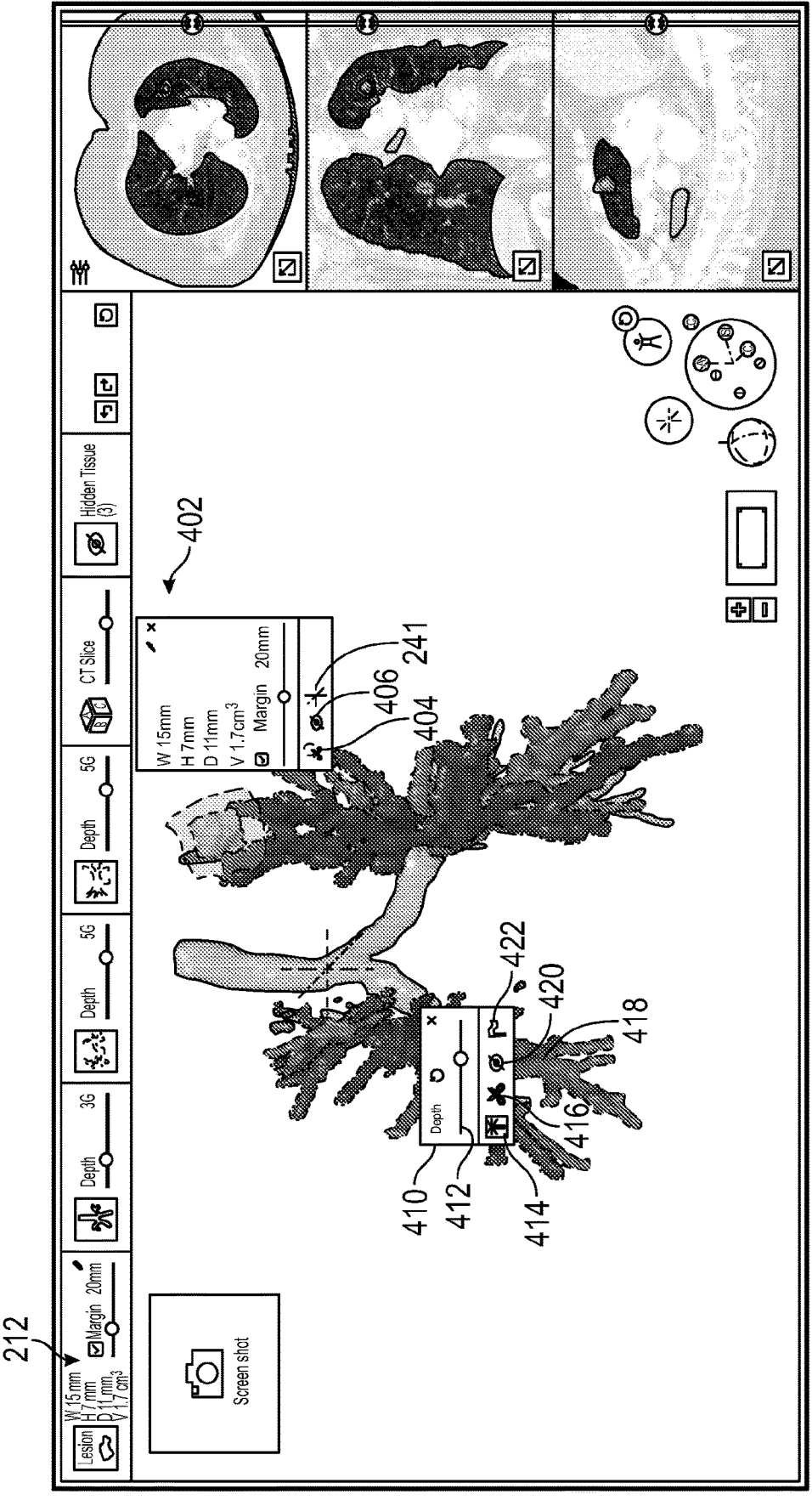
FIG. 4 is a user interface for a thoracic surgery planning platform in accordance with the disclosure.

FIG. 4 depicts further features of the thoracic surgery planning tool. When a user selects the tumor 210, the menu 402 is displayed. As an initial matter, the menu 402 displays the same information as the tumor tool 212. Specifically, the menu 402 may display the dimensions and volume of the tumor. The menu 402 also allows for adjusting the size of the margin around the tumor 210 and elimination of the margin all together.

Figure 5:
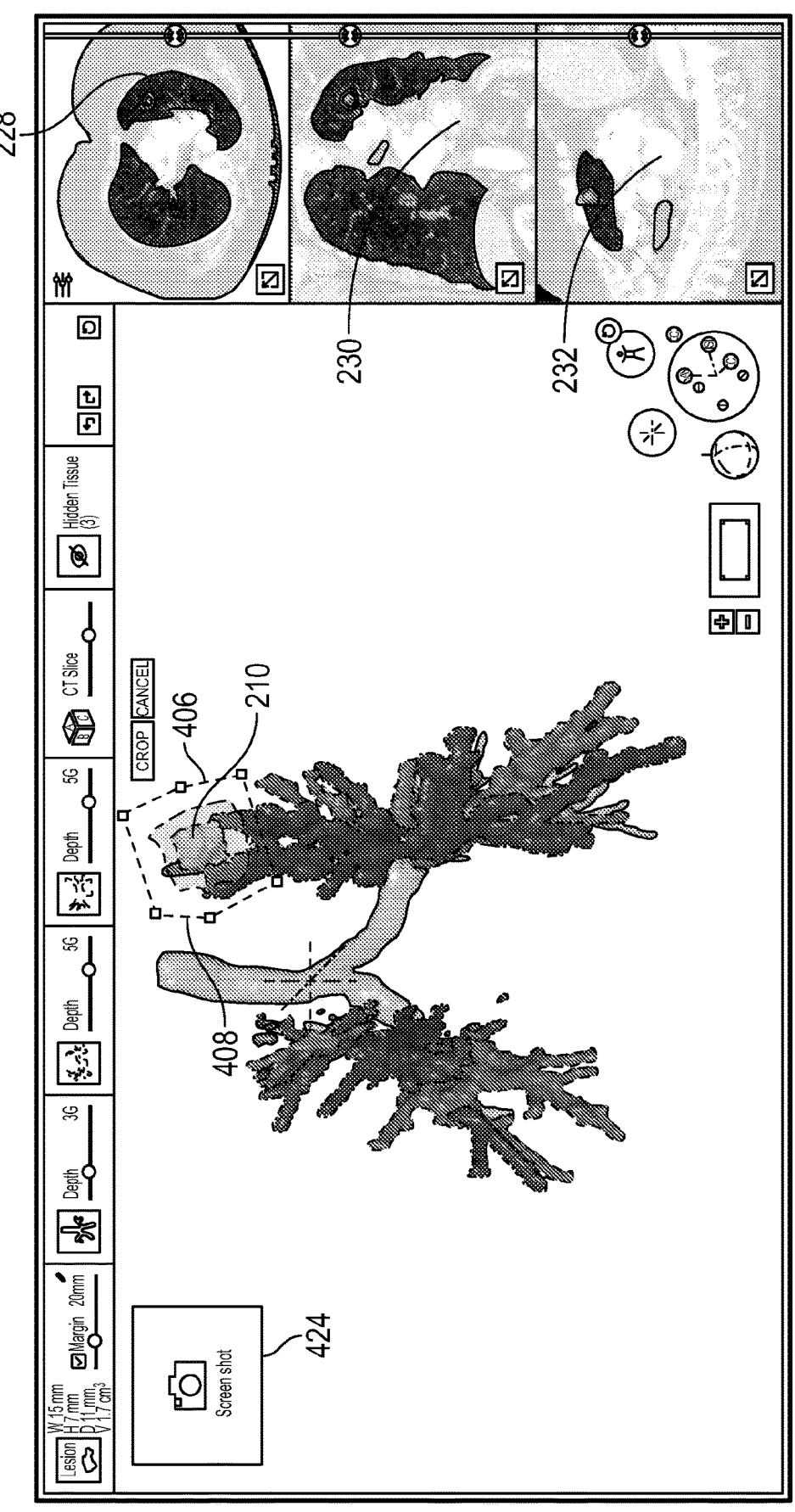
FIG. 5 is a user interface for a thoracic surgery planning platform in accordance with the disclosure.

A crop tool 404 is also provided for in the menu 402. When selected the crop tool defines a region 406 around the tumor 210 as shown in FIG. 5. This region 406 is defined by a series of line segments 408. The user is able to select these line segments 408 to adjust the region 406 around the tumor 210. Once satisfied with the placement of the line segments 408 to define the region 406, the user may select the "crop" button. This removes from the 3D model all tissue that is either not found within the region 406, or is not part of an airway or blood vessel, which passes through the region 406. As with the generation selection tools, described above, the effect of this cropping is that not only are the blood vessels and airways that are within the region 406 displayed so the user can observe them and their relation to the tumor 210, but also displayed are the airways and blood vessels which lead to the airways and blood vessels that are within the region 406.

One of the benefits of this tool is to be able to identify the root branches of the airways and blood vessels leading to the tumor 210. This is made possible by removing all of the clutter caused by the other objects (e.g., airways and blood vessels) of the 3D model that are not related to the cropped region. This allows the user to consider the airways and blood vessels leading to the tumor 210 and determine which segments are implicated by the tumor 210 and which airways and blood vessels might need resection in order to achieve a successful segmentectomy. In this manner the clinician can adjust the size of the margin to identify the relevant blood vessels and airways to minimize the area for resection.

The region 406 may be depicted in the CT image slices 228, 230, 232. Similarly, the tissue that has been cropped from the 3D model may also be cropped in the CT image slices. Further, the tissue that is hidden by the crop selection may not be completely hidden but may be ghosted out to limit the visual interference but leave the clinician able to ascertain where that structure is in the 3D model 202.

FIG. 4 depicts two additional features in the menu 402. One feature is a hide tissue button 408 which when selected hides the tumor 210 and any tissue that is within the margin. Further the anchoring tool 241 is also displayed in the menu allowing selection and placement of the anchor point for the orientation compass 240, as described above.

A second menu 410 may be displayed by the user using the pointing tool to select any location within the 3D model 202. The menu 410 includes a depth slider 412 which is enabled by selecting a button 414 shaped like a palm tree allows the user to change the number of generations related to a tissue at the selected point. This allows for local decluttering around the point selected. Additional features in menu 410 include a clip button 416 which provides an indication of the tissue to be excised in the surgical procedure. By selecting the clip button 416, the user may then use the pointing device to select a location on the 3D model 202. A resection line 418 is drawn on the model at that point and the portions of the 3D model to be resected are presented in a different color. A hide tissue button 420 allows for the selection of tissue using the pointing device and hiding the selected tissue from view to again assist in decluttering the 3D model. A flag button 422 allows for placement of a flag at a location in the 3D model with the pointing device and for the insertion of notes related to that flag.

Figure 6:
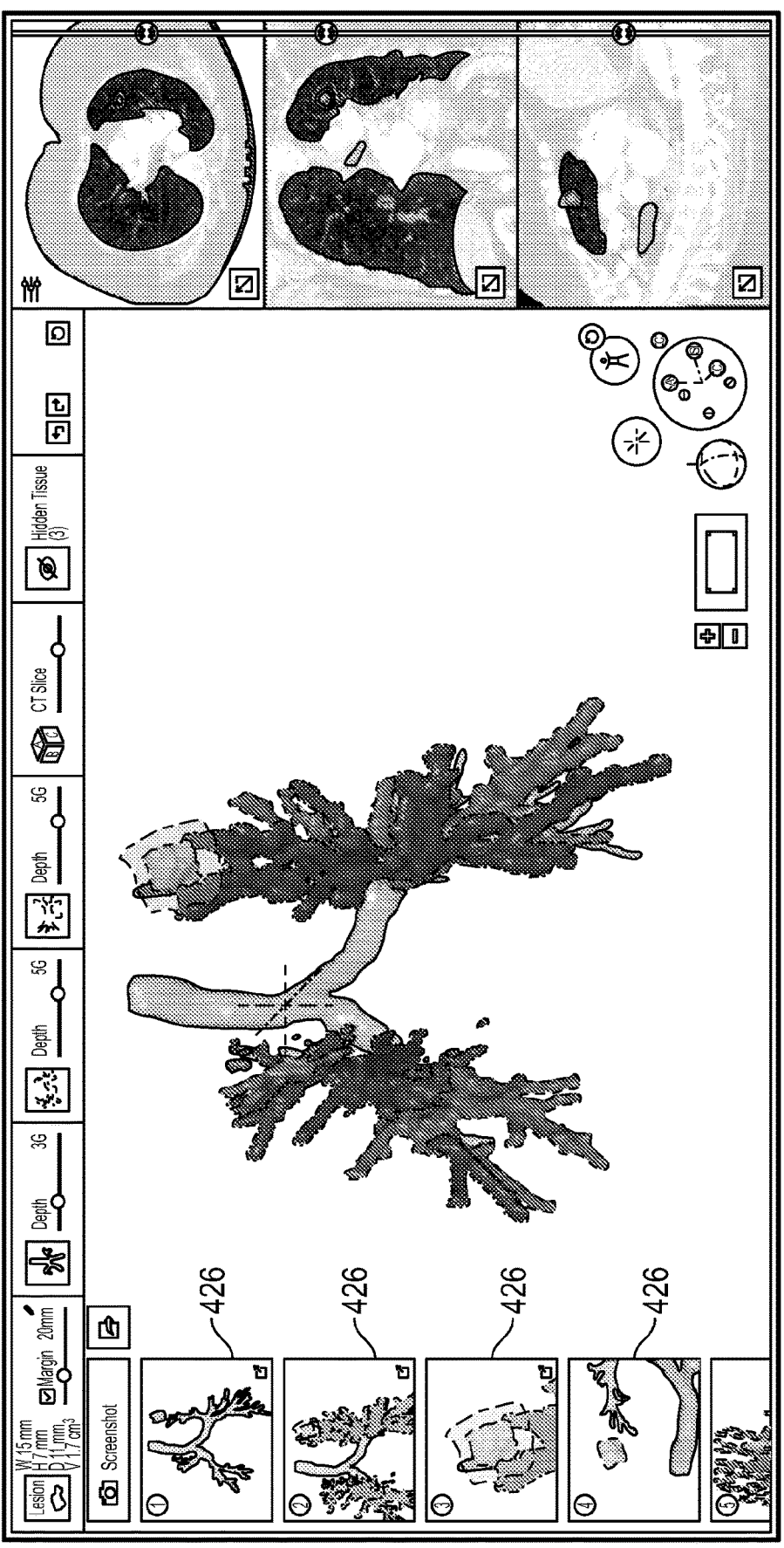
FIG. 6 is a user interface for a thoracic surgery planning platform in accordance with the disclosure.

FIGS. 5 and 6 depict a further aspect of the thoracic surgery planning tool in UI 200. Through any of the manipulations described above where tissue is hidden or cropped or the 3D model 202 is rotated a screenshot may be taken by placing the pointing device on the screen shot icon 424. This may be done many times during the thoracic surgery planning as shown in FIG. 6 with screenshots 426 depicted along the left-hand margin of the UI 200. Each of these screen shots shows some prior manipulation of the 3D model 202. For example, screenshot 1 shows just the airways and the tumor 310. In contrast, screenshot 3 shows a zoomed in image of the tumor 210 and related vasculature. Selection of one of these screenshots reverts the 3D model 202 to the model as it appeared in the screenshot 426. In this way during a procedure the clinician can request that a particular screen shot 426 is displayed to refresh their recollection of the expected tissue in a given area or to assist them in identifying the tissue in-vivo so they can proceed with a given resection with confidence that they are cutting or stapling in the correct location. Or that they have accounted for all of the vasculature related to a particular resection prior to making any cuts or stapling. The clinician can arrange these screen shots so that they follow the intended procedure and the information that the clinician seeks to have available during different portions of the procedure. This also allows for a clinician to plan multiple resections and to store each of those plans for multiple tumors in one set of lungs. Further, when one screen shot is selected for viewing, it can be further edited, and this further edited screenshot can be saved separately or used to update the screenshot.

Though described generally herein as a thoracic surgical planning, the software applications described herein are not so limited. As one example, the UI 200 may be shown herein in the surgical room on one or more monitors. The clinician may then direct surgical staff to select screenshots 426 so that the clinician can again observe the 3D model 202 and familiarize themselves with the structures displayed in the screen shot 426 to advise them on conducting further steps of the procedure.

In accordance with another aspect of the disclosure, the UI 202 may be displayed as part of an augmented reality. Further, they may be displayed in an augmented reality (AR) or virtual reality (VR) systems. For example, the UI 200, and particularly the 3D model 202 may be displayed on a headset or goggles worn by the clinician. The display of the 3D model 202 may be registered to the patient. Registration allows for the display of the 3D model 202 to be aligned with the physiology of the patient. Again, this provides greater context for the clinician when performing the procedure and allows for incorporating the plan into the surgical procedure. Alternatively, the UI 200 and the 3D model 202 may be projected such that it appears on the patient such that the 3D model 202 overlays the actual tissue of the patient. This may be achieved in both open and laparoscopic procedures such that the 3D model provides guidance to the clinician during the procedure. As will be appreciated, such projection requires an image projector in the surgical suite or associated with the laparoscopic tools.

Yet a further aspect of the disclosure is the incorporation of electromagnetic sensors placed on the surgical tools. An electromagnetic field generator located either below or proximate the patient generates an electromagnetic field. The electromagnetic field can be detected by sensors located in the tools used during the surgical procedure. Again, the 3D model 202 must be registered to the patient such that the orientation of the 3D model corresponds to the orientation of the relevant tissue in the patient, for example the lungs. With the registration complete, movement of the surgical tools with the EM field sensors can be detected and displayed on the 3D model 202. In this manner, as the surgical tools are placed proximate tissue within the patient, their positions can also be shown relative to the 3D model 202. In this manner while the surgeon is observing the actual tissue and interacting with it via the surgical tools, the UI 200 displays a model of the tool interacting with the 3D model 202. This allows the surgeon to observe the relative placement of the surgical tools and tissue such as blood vessels and airways that cannot be observed by the surgeon using laparoscopes or during open surgeries.

Figure 7:
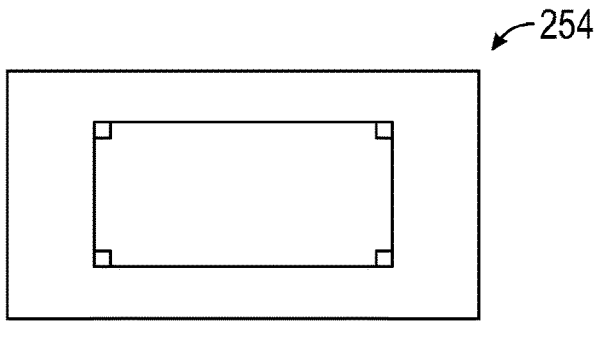
FIG. 7 is an icon appearing in the user interfaces of the thoracic surgery planning platform in accordance with the disclosure.
Figure 8:
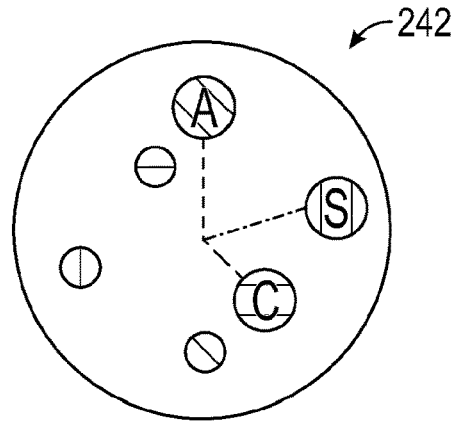
FIG. 8 is an icon appearing in the user interfaces of the thoracic surgery planning platform in accordance with the disclosure.
Figure 9:
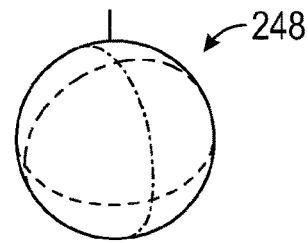
FIG. 9 is an icon appearing in the user interfaces of the thoracic surgery planning platform in accordance with the disclosure.
Figure 10:
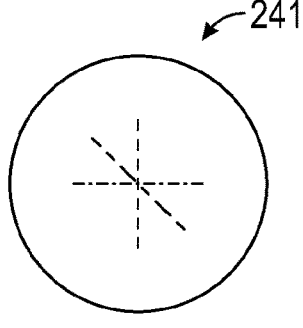
FIG. 10 is an icon appearing in the user interfaces of the thoracic surgery planning platform in accordance with the disclosure.
Figure 11:
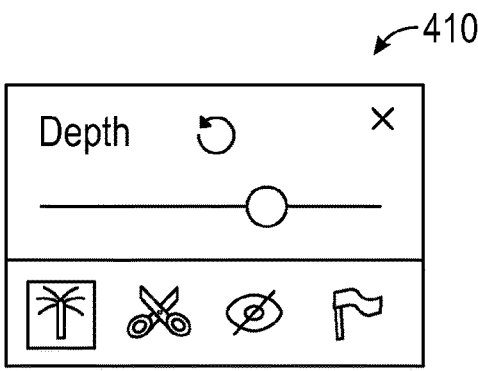
FIG. 11 is an icon appearing in the user interfaces of the thoracic surgery planning platform in accordance with the disclosure.
Figure 12:
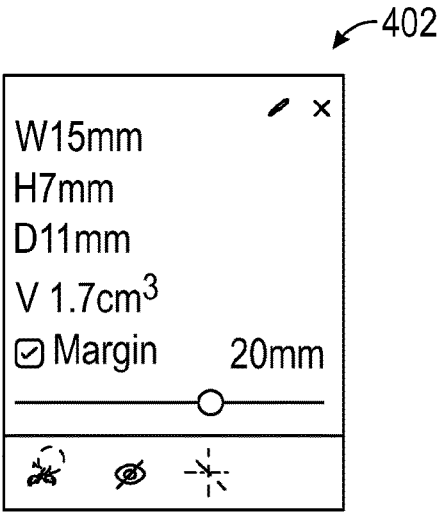
FIG. 12 is an icon appearing in the user interfaces of the thoracic surgery planning platform in accordance with the disclosure.
Figure 13:
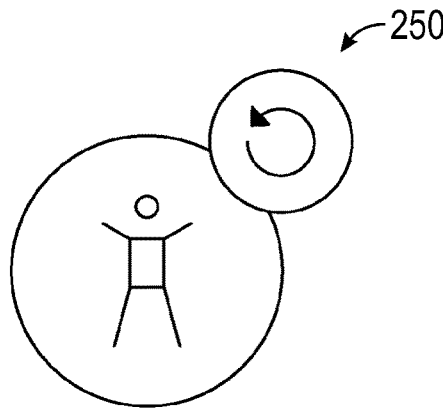
FIG. 13 is an icon appearing in the user interfaces of the thoracic surgery planning platform in accordance with the disclosure.

FIGS. 7-13 are enlarged, and isolated views of the icons discussed above in connection with the UI 200. FIG. 7 depicts the zoom indicator 254. FIG. 8 depicts the axial tool 242. FIG. 9 depicts the single axis rotation tool 248. FIG. 10 depicts the anchoring tool 241. FIG. 11 depicts the menu 410. FIG. 12 depicts the menu 402. FIG. 13 depicts a 3D model orientation tool 250.

Figure 14:
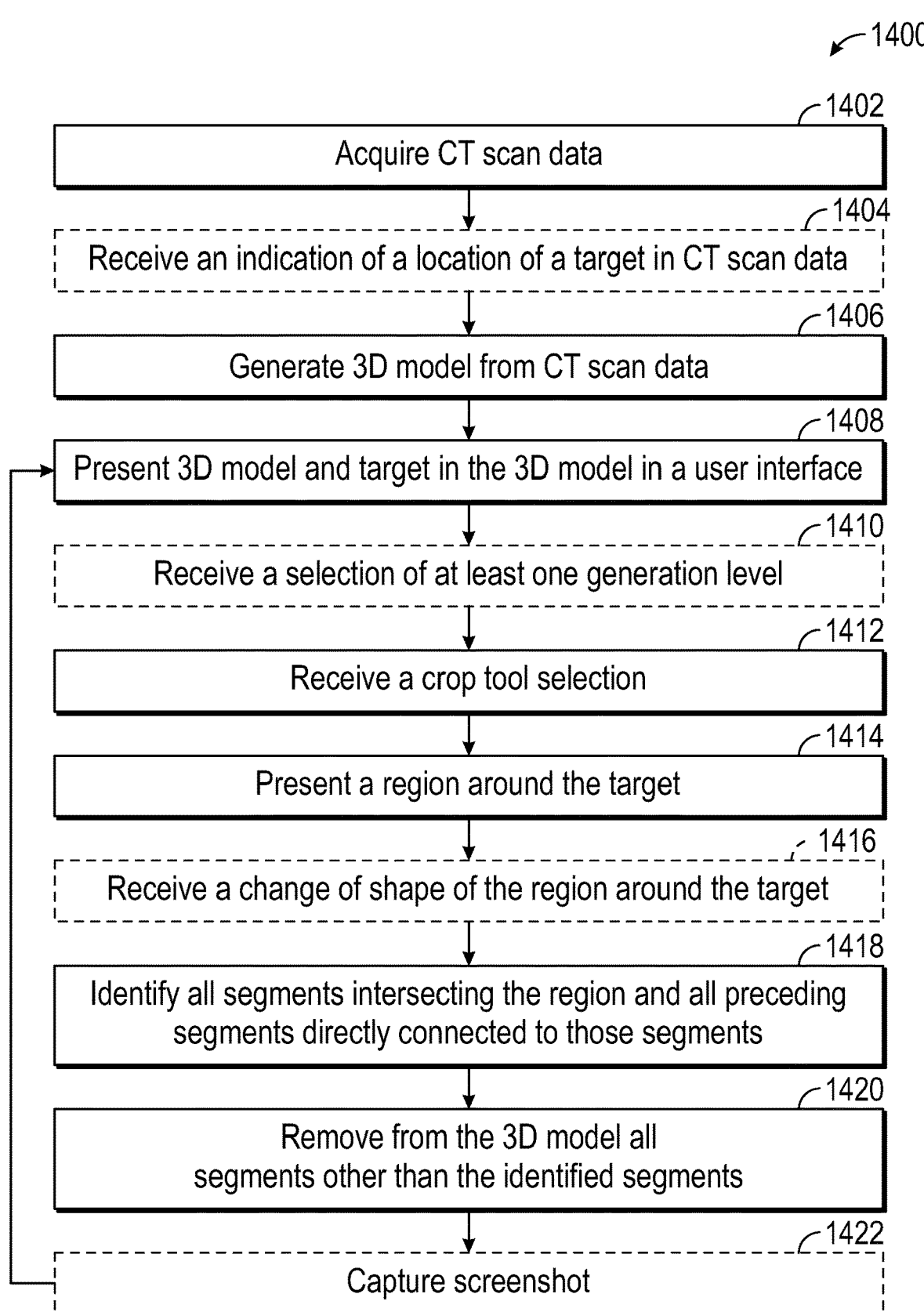
FIG. 14 is a flowchart of a workflow for the thoracic surgery planning platform in accordance with the disclosure.

FIG. 14 depicts a method 1400 of using the thoracic surgery planning application of the disclosure. The method starts with step 1402 of acquiring CT scan data at step 1402. An optional step 1404 is to receive an indication of the location of a target (e.g., a tumor) in the CT scan data. At step 1406 a 3D model is generated from the CT scan data and presented in a user interface at step 1408. The application may optionally receive a selection of a generation level at step 1410. This is the generation level of the airways or the blood vessels. The generation level refers to the level of the luminal network to which the 3D model 202 is displayed. For example, in the airways, the trachea defines a generation 0 and the main bronchus, which follows the main carina or first bifurcation, defines generation 1. Each successive bifurcation may then define a new generation. Though as described in detail above, this disclosure contemplates an alternative algorithm for determining whether an airway. Regardless which generation defining algorithm is employed, reducing the generation level can reduce the clutter in the 3D model and provide better insight for the clinician on interrelated airways and blood vessels when planning a segmentectomy. At step 1412 a selection of a crop tool may be received. This results in displaying a region around the target at step 1414. This region may optionally be adjusted, and changes of the shape may be received at step 1416. At step 1418 all airways and blood vessels of the 3D model which intersect the region can be identified along with the portions of those airways and blood vessels which lead to those airways and blood vessels that intersect the region. At step 1420, all airways and blood vessels which were not identified in step 1418 can be removed from the 3D model. This provides a clear indication of both the blood vessels and the airways which both lead to the target and which are within the region. With this information a more exact determination can be made for the resection and stapling of a segment to remove the diseased tissue without affecting the blood supply to other segments. In addition, these steps can inform on the approach to a procedure and other aspects that are of benefit to the clinician. At step 1422, screenshot 426 may be captured. The user may then revert back to the original 3D model 202 and step 1408. This enables the clinician to perform additional manipulations of the 3D model 202 to develop further aspects of the procedure.

Figure 15:
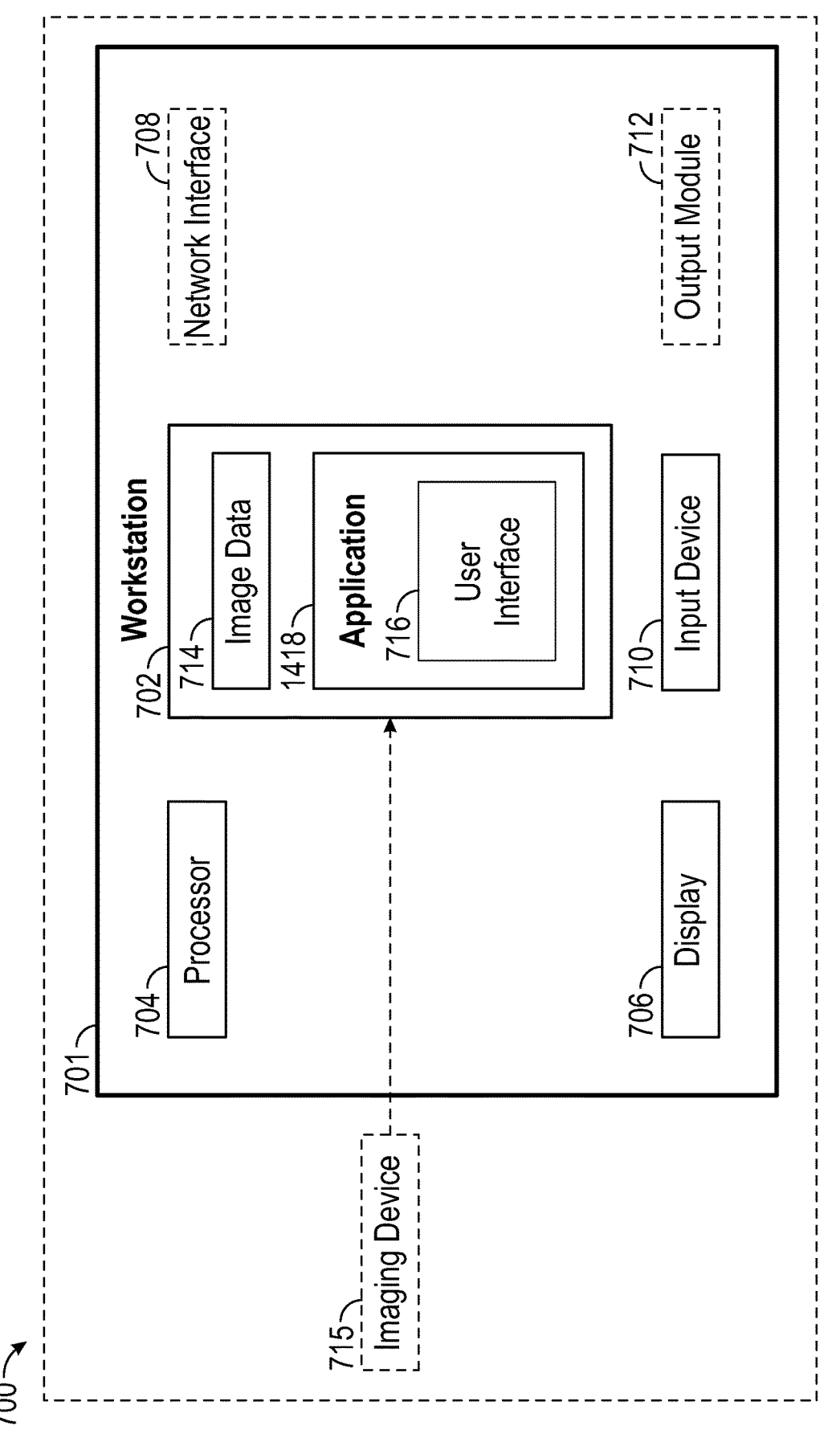
FIG. 15 is a schematic view of a workstation in accordance with the disclosure.

Reference is now made to FIG. 15, which is a schematic diagram of a system 700 configured for use with the methods of the disclosure including the method of FIG. 14. System 700 may include a workstation 701, and optionally an imaging device 715 (e.g., a CT or MM imaging device). In some embodiments, workstation 701 may be coupled with imaging device 715, directly or indirectly, e.g., by wireless communication. Workstation 701 may include a memory 702, a processor 704, a display 706 and an input device 710. Processor or hardware processor 704 may include one or more hardware processors. Workstation 701 may optionally include an output module 712 and a network interface 708. Memory 702 may store an application 718 and image data 77. Application 718 may include instructions executable by processor 704 for executing the methods of the disclosure including the method of FIG. 14.

Application 718 may further include a user interface 716 such as UI 200 described in detail above. Image data 714 may include the CT image scans or MM image data. Processor 704 may be coupled with memory 702, display 706, input device 710, output module 712, network interface 708 and imaging device 715. Workstation 701 may be a stationary computing device, such as a personal computer, or a portable computing device such as a tablet computer. Workstation 701 may embed a plurality of computer devices.

Memory 702 may include any non-transitory computer-readable storage media for storing data and/or software including instructions that are executable by processor 704 and which control the operation of workstation 701 and, in some embodiments, may also control the operation of imaging device 715. In an embodiment, memory 702 may include one or more storage devices such as solid-state storage devices, e.g., flash memory chips. Alternatively, or in addition to the one or more solid-state storage devices, memory 702 may include one or more mass storage devices connected to the processor 704 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 704. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 701.

Application 718 may, when executed by processor 704, cause display 706 to present user interface 716. An example of the user interface 716 is US 200 shown, for example, in FIGS. 2-7.

Network interface 708 may be configured to connect to a network such as a local area network (LAN) consisting of a wired network and/or a wireless network, a wide area network (WAN), a wireless mobile network, a Bluetooth network, and/or the Internet. Network interface 708 may be used to connect between workstation 701 and imaging device 715. Network interface 708 may be also used to receive image data 714. Input device 710 may be any device by which a user may interact with workstation 701, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

Any of the above aspects and embodiments of the present disclosure may be combined without departing from the scope of the present disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A method of planning a thoracic surgery comprising:
receiving computed tomography (CT) image data;
receiving an indication of a location of a suspected tumor in the CT image data;
generate a three-dimensional model (3D) from the CT image data;
display the 3D model in a user interface;
receiving an input via the user interface of selection of a generation level of the 3D model;
removing from the displayed 3D model in a user interface the generations beyond the selected generation level;
receiving a selection of a crop tool to crop the 3D model to a region around a suspected tumor in the 3D model;
presenting the region of the 3D model around the suspected tumor;
receiving a change in dimensions of the region of the 3D model around the suspected tumor;
identifying all airways and blood vessels of the 3D model entering the changed region and all preceding airways and blood vessels directly connected to the airways and blood vessels in the 3D model to form identified airways and blood vessels; and
removing from the 3D model all airways and blood vessels other than the identified airways and blood vessels.

2. A method of planning a thoracic surgery comprising:
receiving computed tomography (CT) image data;
generating a three-dimensional model (3D) from the CT image data;
displaying the 3D model;
receiving an input selecting a generation level of the 3D model and removing generations from the 3D model beyond the selected generation level;
removing from the displayed 3D model the generations beyond the selected generation level;
receiving a selection of a crop tool to crop the 3D model to a region around a suspected tumor in the 3D model;
presenting the region of the 3D model around the suspected tumor;
identifying all airways and blood vessels of the 3D model entering the region and all preceding airways and blood vessels directly connected to the airways and blood vessels entering the region in the 3D model;
removing from the 3D model all airways and blood vessels other than the identified airways and blood vessels; and displaying the 3D model in a user interface, wherein the 3D model includes only the identified airways and blood vessels.

3. The method of claim 2, further comprising receiving an indication of a location of a suspected tumor in the CT image data.

4. The method of claim 2, further comprising determining a generation by identifying a bifurcation of an airway or blood vessel and determining a diameter of an airway or blood vessel leading to the bifurcation and a diameter of airways or blood vessels extending beyond the bifurcation, wherein one of the airways or blood vessels extending from the bifurcation considered the same generation as the airway or blood vessel leading to the bifurcation when the determined diameters are similar in size.

5. The method of claim 4, further comprising determining that an airway or blood vessel extending from a bifurcation is at a next generation when that airway or blood vessel's diameter less than 50% of the diameter of the airway or blood vessel leading to the bifurcation.

6. The method of claim 2, further comprising receiving a change in shape of the region around the suspected tumor.

7. The method of claim 2, further comprising capturing a screenshot.

8. The method of claim 2 further comprising at least one CT image, wherein the CT image is tied to the 3D model such that manipulation of the 3D model results in corresponding changes to the display of the CT image.

9. The method of claim 2, further comprising segmenting airways and blood vessels in the CT image data to generate the 3D model.

10. A thoracic surgery planning system comprising:
a processor;
a display in communication with the processor; and
a memory in communication with the processor, wherein the memory stores therein executable code that when executed by the processor generate a user interface (UI) for display on the display, the user interface including,
a three-dimensional (3D) model of airways and vasculature of a patient's lungs;
at least one generation tool configured to limit a number of generations of the 3D model displayed, wherein upon receipt of an input via the user interface of a generation level removes from the displayed 3D model in a user interface generations of the 3D model beyond a selected generation level;

a margin tool configured to adjust a displayed margin around a suspected tumor;
a plurality of orientation manipulation tools configured to alter a view of the 3D model presented in the UI; and
a crop tool, which when selected, crops the 3D model presented in the UI to a region around the suspected tumor.

11. The thoracic surgery planning system of claim 10, wherein the memory is configured to receive CT image scan data and the processor is configured executed code stored in the memory to generate the 3D model from the CT image scan.

12. The thoracic surgery planning system of claim 10, wherein the UI includes an orientation compass identifying axial, coronal, and sagittal planes of 3D model.

13. The thoracic surgery planning system of claim 12, further comprising an anchoring tool, wherein the anchoring tool enables placement of the orientation compass on or near the 3D model to define a point of rotation of the 3D model.

14. The thoracic surgery planning system of claim 10, further comprising a single axis rotation tool, wherein when one of the axes in the single axis selection to is selected, all further inputs to rotate the 3D model achieve rotation only about the selected axis.

15. The thoracic surgery planning system of claim 10, further comprising a zoom tool, wherein the zoom tool depicts a relative size of the presented model in the UI compared to full size.

16. The thoracic surgery planning system of claim 15, wherein the zoom tool also enables panning of the 3D model in the UI.

17. The thoracic surgery planning system of claim 10, wherein the region is adjustable such that segments of airways or blood vessels are included or excluded from the region.

18. The thoracic surgery planning system of claim 17, wherein when the crop is executed the processor executes code to determine the airways or blood vessels which are within the region and any of their preceding airways or blood vessels, and the 3D model is updated to eliminate all airways or blood vessels except for the identified airways or blood vessels.

* * * * *